(12) United States Patent
Park et al.

(10) Patent No.: US 9,200,027 B2
(45) Date of Patent: Dec. 1, 2015

(54) DRIED OLIGONUCLEOTIDE COMPOSITION AND METHOD OF PRODUCING THE SAME

(75) Inventors: Han Oh Park, Daejeon (KR); Jae Ha Kim, Daejeon (KR)

(73) Assignee: BIONEER CORPORATION, Daejeon (KR)

(*) Notice: Subject to any disclaimer, the term of this patent is extended or adjusted under 35 U.S.C. 154(b) by 582 days.

(21) Appl. No.: 12/279,431

(22) PCT Filed: Feb. 7, 2007

(86) PCT No.: PCT/KR2007/000662
§ 371 (c)(1),
(2), (4) Date: Aug. 14, 2008

(87) PCT Pub. No.: WO2007/094581
PCT Pub. Date: Aug. 23, 2007

(65) Prior Publication Data
US 2009/0023906 A1      Jan. 22, 2009

(30) Foreign Application Priority Data
Feb. 14, 2006   (KR) .................. 10-2006-0014126

(51) Int. Cl.
*C07H 21/00* (2006.01)
*C12Q 1/68* (2006.01)

(52) U.S. Cl.
CPC ..................................... *C07H 21/00* (2013.01)

(58) Field of Classification Search
None
See application file for complete search history.

(56) References Cited

U.S. PATENT DOCUMENTS

| 6,214,621 | B1 | 4/2001 | Betbeder et al. |
| 6,262,251 | B1 | 7/2001 | Pieken et al. |
| 2002/0045582 | A1* | 4/2002 | Margolin et al. ................ 514/21 |
| 2003/0026840 | A1* | 2/2003 | Plank et al. .................... 424/486 |
| 2003/0101995 | A1* | 6/2003 | Yamashita et al. ........ 128/203.15 |
| 2003/0148979 | A1* | 8/2003 | Sosnowski et al. ............. 514/44 |
| 2004/0042972 | A1* | 3/2004 | Truong-Le et al. ............. 424/46 |
| 2005/0276728 | A1* | 12/2005 | Muller-Cohn et al. ....... 422/102 |

FOREIGN PATENT DOCUMENTS

| JP | 1-308231 | A | 12/1989 |
| JP | 7227284 | A2 | 8/1995 |
| JP | 8-511956 | A | 12/1996 |
| JP | 2001-516329 | A | 9/2001 |
| JP | 2002-506048 | A | 2/2002 |
| WO | 01/97857 | A1 | 12/2001 |
| WO | 2004/060059 | A2 | 7/2004 |

OTHER PUBLICATIONS

Darst et al, The EMBO Journal, vol. 20, pp. 2028-2040 (2001).*

* cited by examiner

*Primary Examiner* — Robert T Crow
(74) *Attorney, Agent, or Firm* — Rothwell, Figg, Ernst & Manbeck, P.C.

(57) ABSTRACT

The present invention relates to a dried oligonucleotide composition and a method for producing the same. More specifically, it relates to a dried oligonucleotide composition produced by the steps comprising adding a substance for preventing the oligonucleotide from being separated and lost, which is adhesive to a storage container containing the oligonucleotide composition, in order to prevent the oligonucleotide from being separated and lost during manufacturing and distributing the dried oligonucleotide composition, optionally adding a non-reactive dye substance, and drying the resulting solution. The dried oligonucleotide composition of the present invention can be prevented from being separated and lost during manufacturing step, or transporting step after packaging, and the presence or absence of the oligonucleotide in the storage container can be easily confirmed with naked eyes. Accordingly, unnecessary labor waste and time waste caused by the separation of the oligonucleotide upon experiment can be overcome.

11 Claims, 2 Drawing Sheets

```
                          SEQUENCE LISTING

<160> NUMBER OF SEQ ID NOS: 4

<210> SEQ ID NO 1
<211> LENGTH: 20
<212> TYPE: DNA
<213> ORGANISM: Unknown
<220> FEATURE:
<223> OTHER INFORMATION: synthetic oligonucleotide primer (forward)

<400> SEQUENCE: 1
aatatgagcc agcggggatt                                                   20

<210> SEQ ID NO 2
<211> LENGTH: 20
<212> TYPE: DNA
<213> ORGANISM: Unknown
<220> FEATURE:
<223> OTHER INFORMATION: synthetic oligonucleotide primer (reverse)

<400> SEQUENCE: 2
catccagaaa acgggcgtaa                                                   20

<210> SEQ ID NO 3
<211> LENGTH: 23
<212> TYPE: DNA
<213> ORGANISM: Unknown
<220> FEATURE:
<223> OTHER INFORMATION: synthetic siRNA oligonucleotide (sense)
<220> FEATURE:
<221> NAME/KEY: misc_feature
<222> LOCATION: (22)..(23)
<223> OTHER INFORMATION: thymine is connected at the 3'-end of the siRNA
      oligonucleotide
```

-continued

```
<400> SEQUENCE: 3
ccaaguaacu cuccucaaau att                                               23

<210> SEQ ID NO 4
<211> LENGTH: 23
<212> TYPE: DNA
<213> ORGANISM: Unknown
<220> FEATURE:
<223> OTHER INFORMATION: synthetic siRNA oligonucleotide (antisense)
<220> FEATURE:
<221> NAME/KEY: misc_feature
<222> LOCATION: (22)..(23)
<223> OTHER INFORMATION: thymine is connected at the 3'-end of the siRNA
      oligonucleotide

<400> SEQUENCE: 4
uauuugagga gaguuacuug gtt                                               23
```

DRIED OLIGONUCLEOTIDE COMPOSITION AND METHOD OF PRODUCING THE SAME

CROSS REFERENCE TO RELATED APPLICATIONS

This application is a 35 USC §371 National Phase Entry Application from PCT/KR2007/000662, filed Feb. 7, 2007, and designating the United States. This application claims priority under 35 U.S.C. §119 based on Korean Patent Application No. 10-2006-0014126 filed Feb. 14, 2006, which is incorporated herein in its entirety.

FIELD OF THE INVENTION

The present invention relates to a dried oligonucleotide composition and a method of producing the same. More specifically, it relates to a dried oligonucleotide composition which can prevent the oligonucleotide from being separated and lost out of a container during drying and/or transporting the oligonucleotide, and a method of producing the same.

DESCRIPTION OF THE RELATED ART

After completion of a human genome project, researches for human genes have thoroughly been undergoing. Thus, the amount of the oligonucleotide which is essential for the studies on the function of genes, single nucleotide polymorphism (SNP), gene chips, gene-based drug discovery, or the like tends to be greatly increased.

Since a first chemical synthesis of oligonucleotide in 1967 (Khorana, Proceedings of the Seventh International Congress of Biochemistry, Tokyo, 1967, p. 17), the synthetic process has been still further improving. A process for industrial production of the oligonucleotide consists of the steps of synthesis, recovery, purification, quantitation, drying and packaging. In the first step for synthesizing oligonucleotide, the oligonucleotide is synthesized using a solid silica support by sequentially adding adenosine, guanosine, cytidine and thymidine, each of which is an essential base material constituting a gene. The nucleotides are added via four sequential reaction steps, that is, a de-blocking reaction, a coupling reaction, a capping reaction and an oxidation reaction to make desired oligonucleotide. After completion of the oligonucleotide synthesis, it is followed by a recovery step for detaching the oligonucleotide from the solid support. In this step, the oligonucleotide is recovered by the reaction with aqueous ammonia at 90° C. for more than 2 hours. Then, in a third step, the synthesized oligonucleotide is purified using a reversed phase silica resin via chromatographic method. By the purification step, impurities other than the oligonucleotide are removed. It is followed by a quantitation step, in which the absorbance of the oligonucleotide is measured using a UV spectrophotometer, and the number of moles of the synthesized oligonucleotide is calculated. Thereafter, the oligonucleotide is divided in portions according to the mole numbers, and is aliquoted into a storage container such as a tube or a plate. The aliquoted oligonucleotide is transferred to a drying step. Finally, the dried oligonucleotide is packaged, labeled, transported, and then delivered to a user.

The oligonucleotide is used, for example, for polymerase chain reaction (PCR). PCR is a reaction for amplifying a desired DNA sequence using two chemically synthesized oligonucleotides (typically referred to as primers) and a DNA polymerase. Since a trace amount of oligonucleotide is used for PCR, the oligonucleotide is packaged in such trace amount per unit, and commercially sold as a commercial product. Accordingly, the commercial oligonucleotide is put into a container in a small amount (ng- to μg-scaled amount). Since very small amounts of the oligonucleotide are used and the appearance of the oligonucleotide is colorless and transparent, it is difficult to confirm the presence or absence of the oligonucleotide with naked eyes while manufacturing and selling the product.

In the case where a dried oligonucleotide product is prepared by aliquoting a trace amount of the oligonucleotide to a storage container and drying it, there is no way to confirm the presence or absence of the oligonucleotide during drying or transporting steps, particularly when the oligonucleotide is separated out of a container or adhered on the lid of the container. If the oligonucleotide is separated out of the container and lost while drying, storing or transporting the oligonucleotide, the amount of the oligonucleotide acting as a primer for PCR becomes insufficient in practice. In this case, a user misunderstands that sufficient amounts of the oligonucleotide are present in the container, and tries to perform PCR. As a result, the PCR fails or is not substantially performed, thereby leading incorrect experimental result. This leads to time waste, cost waste, or labor waste.

SUMMARY OF THE INVENTION

The present invention aims to improve the problems which have conventionally occurred while drying, storing or transporting the oligonucleotide, and thus to provide a dried oligonucleotide composition for preventing the oligonucleotide from being separated and lost while drying, storing or transporting the oligonucleotide, and a method of producing the same.

The present invention provides a dried oligonucleotide composition comprising the oligonucleotide and a substance for preventing the oligonucleotide from being separated and lost, which is adhesive to a storage container containing the oligonucleotide composition.

The present invention further provides a method of producing the dried oligonucleotide composition, comprising the steps of adding one or more adhesive substances for preventing the oligonucleotide from being separated and lost to the oligonucleotide composition, and then drying the oligonucleotide composition.

DETAILED DESCRIPTION OF THE PREFERRED EMBODIMENTS

The present invention may be understood more readily by reference to the following detailed description of the preferred embodiments of the invention and the Examples included herein.

The present invention provides a dried oligonucleotide composition comprising the oligonucleotide and a substance for preventing the oligonucleotide from being separated and lost, which is adhesive to a storage container containing the oligonucleotide composition.

The term, "oligonucleotide", as used herein, means nucleic acid having a relatively short length in the range of one to several hundreds of base pairs, and encompass DNA oligonucleotide, RNA oligonucleotide, siRNA oligonucleotide, and the like. Further, the term, "a storage container" means a container containing the oligonucleotide for commercial distribution after manufacturing the oligonucleotide, and is preferably made from a synthetic resin such as polypropylene, but is not limited thereto.

First, in one instance, the oligonucleotide may be separated and lost while drying a chemically synthesized oligonucleotide in the process of producing oligonucleotide product, as specifically described below. After chemically synthesizing oligonucleotide, an appropriate amount, i.e., 10 µl to 1,000 µl of an oligonucleotide composition dissolved in a liquid state on nanomole scales is aliquoted into a storage container, preferably into a polypropylene storage container, for example, a 2-ml polypropylene tube or a 96-well polypropylene plate. Then, the oligonucleotide composition is dried in the final step of the production process. In the drying step, the storage container, preferably a polypropylene storage container containing the oligonucleotide is dried on a dryer, preferably a vacuum dryer. Here, if it is dried in vacuo on a vacuum dryer for 3 hours or longer, an aqueous buffer solution is evaporated. If the buffer solution is evaporated in the dryer, the oligonucleotide in the dried state is left. In this case, the oligonucleotide can be frequently detached from the polypropylene storage container in the dryer during the drying step. The colorless and transparent appearance of the oligonucleotide and use of a trace amount of the oligonucleotide in nanomole scales make it substantially impossible to confirm the presence of the oligonucleotide with naked eyes. If the oligonucleotide is lost during the drying step, there is no way to confirm the absence of the oligonucleotide. Accordingly, the oligonucleotide products are commercially sold without clearly checking the presence of the oligonucleotide.

In addition, the oligonucleotide can be also separated and lost while storing or transporting the oligonucleotide after the drying step. For example, after the dried oligonucleotide is put into a storage container, it may be detached from the bottom of the polypropylene storage container and adhered to a lid on the upper part of the storage container. In this case, a user believes that oligonucleotide may be present in a tube or a plate, and adds a buffer solution thereinto to dissolve the oligonucleotide for use in experiments such as PCR. Finally, the user would perform an experiment such as PCR without primers, possibly leading to unwanted results of the experiment.

Therefore, the present inventors have conducted extensive studies in order to improve the problem that oligonucleotide is separated and lost during drying, storing or transporting steps, and have found that oligonucleotide can be effectively prevented from being separated and lost during the drying step by adding a certain amount of a substance for preventing the oligonucleotide from being separated and lost to an oligonucleotide composition before the drying step, and then drying the oligonucleotide composition.

The "substance for preventing the oligonucleotide from being separated and lost" should be a material which is adhesive to a storage container, preferably a synthetic resin container, and more preferably a polypropylene storage container, and is chemically non-reactive with the oligonucleotide, and does not give substantive influence on PCR. The present inventors have tried to find a material satisfying the above-described requirements, and have found that the requirements are satisfied by using protein, water soluble polymer, nonionic surfactant, oligosaccharide or polyalcohol singly or in combination. Among them, polyalcohol is preferably used. The substance for preventing the oligonucleotide from being separated and lost can be contained in an amount of 0.01 to 5 parts by weight, preferably 0.01 to 0.5 parts by weight, based on 100 parts by weight of the oligonucleotide. If the content is more than 5 parts by weight, the physical properties of the oligonucleotide are problematically affected, whereas if the content is less than 0.01 parts by weight, the material does not act as an agent for preventing the oligonucleotide from being separated and lost.

The protein can preferably be gelatin, albumin or acetylated albumin singly or in combination thereof, but is not limited thereto. The protein can be contained in an amount of 0.01 to 5 parts by weight, preferably 0.01 to 0.5 parts by weight, based on 100 parts by weight of the oligonucleotide. If the content is more than 5 parts by weight, the physical properties of the oligonucleotide are problematically affected, whereas if the content is less than 0.01 parts by weight, the material problematically does not act as an agent for preventing the oligonucleotide from being separated and lost.

The water soluble polymer can preferably be polyethylene glycol, polyvinyl alcohol, polyacrylic acid, polymethacrylic acid, polyacrylamide, polyvinyl sulfonic acid, polydiallydimethyl ammonium chloride, polyvinyl pyrrolidone, polyoxyethylene, polyvinyl acetate, polyvinylcyanoethyl ether, hydroxyethyl cellulose, cellulose sulfate, amylopectin, polyethylene glycol monomethyl ether or polyethylene glycol tert-octylphenyl ether singly or in combination thereof, but is not limited thereto. The water soluble polymer can be contained in an amount of 0.01 to 5 parts by weight, preferably 0.01 to 0.1 parts by weight, based on 100 parts by weight of the oligonucleotide. If the content is more than 5 parts by weight, the physical properties of the oligonucleotide are problematically affected, whereas if the content is less than 0.01 parts by weight, the water soluble polymer does not act as an agent for preventing the oligonucleotide from being separated and lost.

The nonionic surfactant can preferably be ethylene glycol monolaurate, propylene glycol monolaurate, triglycerol monostearate, polyoxyethylene sorbitan monolaurate, polyoxyethylene sorbitan monopalmitate, polyoxyethylene sorbitan monostearate, polyoxyethylene sorbitan monooleate, methyl glucoside, octyl glucoside, methyl glucoside monolaurate or sorbitol monolaurate singly or in combination thereof, but is not limited thereto. The nonionic surfactant can be contained in an amount of 0.01 to 5 parts by weight, preferably 0.01 to 0.1 parts by weight, based on 100 parts by weight of the oligonucleotide. If the content is more than 5 parts by weight, the physical properties of the oligonucleotide are problematically affected, whereas if the content is less than 0.01 parts by weight, the nonionic surfactant does not act as an agent for preventing the oligonucleotide from being separated and lost.

The oligosaccharide can preferably be fructo oligosaccharide, malto oligosaccharide, isomalto oligosaccharide, galacto oligosaccharide or soybean oligosaccharide singly or in combination thereof, but is not limited thereto. The oligosaccharide can be contained in an amount of 0.01 to 5 parts by weight, preferably 0.01 to 0.5 parts by weight, based on 100 parts by weight of the oligonucleotide. If the content is more than 5 parts by weight, the physical properties of the oligonucleotide are problematically affected, whereas if the content is less than 0.01 parts by weight, the oligosaccharide does not act as an agent for preventing the oligonucleotide from being separated and lost.

The polyalcohol can preferably be ethylene glycol, glycerin, threitol, arabitol, glucose, mannitol, galactitol or sorbitol singly or in combination thereof, but is not limited thereto. The polyalcohol can be contained in an amount of 0.01 to 5 parts by weight, preferably 0.01 to 0.1 parts by weight, based on 100 parts by weight of the oligonucleotide. If the content is more than 5 parts by weight, the physical properties of the oligonucleotide are problematically affected, whereas if the content is less than 0.01 parts by weight, the polyalcohol does not act as an agent for preventing the oligonucleotide from being separated and lost.

Meanwhile, the composition of the present invention can further comprise a dye substance which is non-reactive to the oligonucleotide for providing color to the dried oligonucleotide composition.

As described above, the colorless and transparent appearance of the oligonucleotide makes it difficult to confirm the presence of the oligonucleotide in the polypropylene storage container with naked eyes. Therefore, in the present invention, the presence or absence of the oligonucleotide in the polypropylene storage container can be easily confirmed by adding a certain amount of a non-reactive dye substance with the substance for preventing the oligonucleotide from being separated and lost to an oligonucleotide composition before the drying step in order to make it easier to confirm the presence or absence of the oligonucleotide in the polypropylene container.

The "non-reactive dye substance", as used herein, should be selected from the substance which is chemically non-reactive with the oligonucleotide and the substance for preventing the oligonucleotide from being separated and lost, and do not affect the PCR. Examples of the substance satisfying the requirements include water soluble dyes such as bromophenol blue, xylene cyanole, bromocresol red, and cresol red, and among these, xylene cyanole is preferably used. The non-reactive dye substance can be contained in an amount of 1 ppm to 10,000 ppm, and preferably 1 ppm to 1,000 ppm, based on the oligonucleotide. If the content of the non-reactive dye substance is more than 10,000 ppm, the physical properties of the oligonucleotide can be affected, whereas if the content is less than 1 ppm, the presence or absence of the oligonucleotide in the storage container cannot be discriminated.

Further, the present invention provides a method of producing the dried oligonucleotide composition, comprising the steps of:

1) preparing an oligonucleotide composition containing oligonucleotide, and one or more substance for preventing the oligonucleotide from being separated and lost, selected from the group consisting of protein, water soluble polymer, nonionic surfactant, oligosaccharide and polyalcohol; and
2) drying the resulting solution.

The substance for preventing the oligonucleotide from being separated and lost can be one or more substance selected from the group consisting of protein, water soluble polymer, nonionic surfactant, oligosaccharide and polyalcohol singly or in combination thereof, as described above. Among these, polyalcohol is preferably used.

In the present invention, the dried oligonucleotide composition can be aliquoted into a storage container after the step 1) or 2). Specifically, in the case of aliquoting the dried oligonucleotide composition into the storage container after the step 1), a predetermined amount of the oligonucleotide composition is aliquoted first into a synthetic resin container, preferably a polypropylene container, and then a substance for preventing the oligonucleotide from being separated and lost is added to each container. After that, drying step is performed. Whereas, in the case of aliquoting the dried oligonucleotide composition into the storage container after the step 2), a mixed solution obtained by adding one or more substance for preventing the oligonucleotide from being separated and lost to an oligonucleotide composition is prepared, and then a predetermined amount of the oligonucleotide composition is aliquoted into a synthetic resin container. After that, drying step is performed. The synthetic resin container, as used herein, can have various shapes such as a plate, tube or bottle, but is not limited thereto.

Further, the dried oligonucleotide composition of the present invention can be prepared by adding an effective amount of a non-reactive dye substance to the oligonucleotide composition, and then drying it. As the non-reactive dye substance, a water soluble dye such as bromophenol blue, xylene cyanole, bromocresol red, and cresol red may be used, and among these, xylene cyanole can preferably be used.

Lane M; molecular weight standards of 1 kb (ladder),
Lanes 1, 2 and 3; control compositions without addition of a substance for preventing the oligonucleotide from being separated and lost,
Lanes 4, 5 and 6; compositions with addition of a 0.25% (v/v) glycerin,
Lanes 7, 8 and 9; control compositions without addition of a substance for preventing the oligonucleotide from being separated and lost,
Lanes 10, 11 and 12; compositions with addition of a 0.25% (v/v) polyoxyethylene sorbitan monolaurate.

Figure 2:
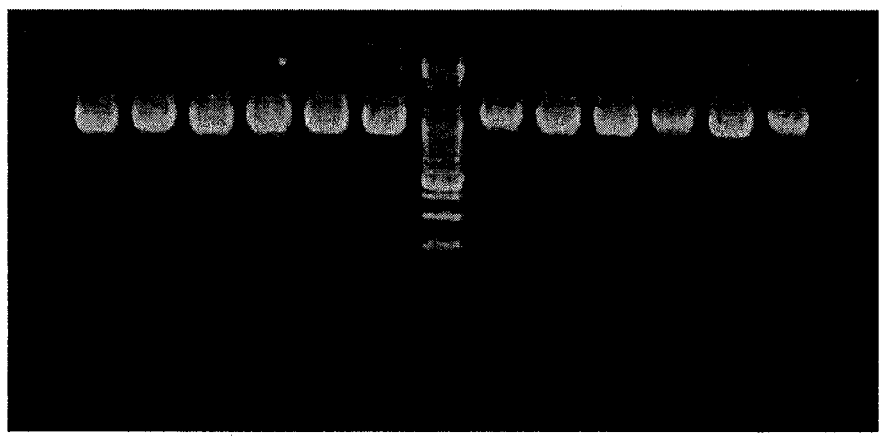

FIG. 2 is a photograph illustrating the results of agarose gel electrophoresis of the reaction product amplified by PCR, in the cases where a substance for preventing the oligonucleotide from being separated and lost is not added to the oligonucleotide, and where isomalto oligosaccharide or polyethylene glycol (PEG) is added to the oligonucleotide.

Lane M; molecular weight standards of 1 kb (ladder),
Lanes 1, 2 and 3; control compositions without addition of a substance for preventing the oligonucleotide from being separated and lost,
Lanes 4, 5 and 6; compositions with addition of a 0.25% (v/v) isomalto oligosaccharide solution,
Lanes 7, 8 and 9; control compositions without addition of a substance for preventing the oligonucleotide from being separated and lost,
Lanes 10, 11 and 12; compositions with addition of a 0.1% (w/v) polyethylene glycol.

Figure 3:
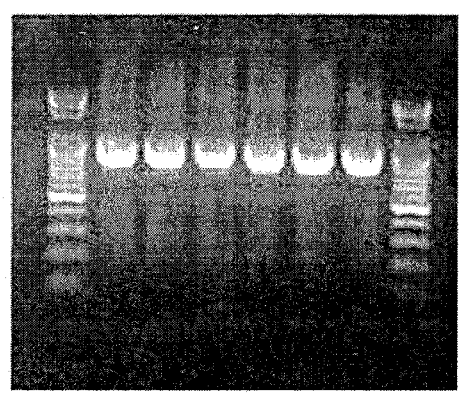

FIG. 3 is a photograph illustrating the results of agarose gel electrophoresis of the reaction product amplified by PCR, in the cases where a substance for preventing the oligonucleotide from being separated and lost is not added to the oligonucleotide, and where the substance for preventing the oligonucleotide from being separated and lost is added to the oligonucleotide, wherein the substance for preventing the oligonucleotide from being separated and lost is bovine serum albumin (BSA).

Lane M; molecular weight standards of 1 kb (ladder),
Lanes 1, 2 and 3; control compositions without addition of a substance for preventing the oligonucleotide from being separated and lost,
Lanes 4, 5 and 6; compositions with addition of a 0.05% (w/v) BSA.

Figure 4:
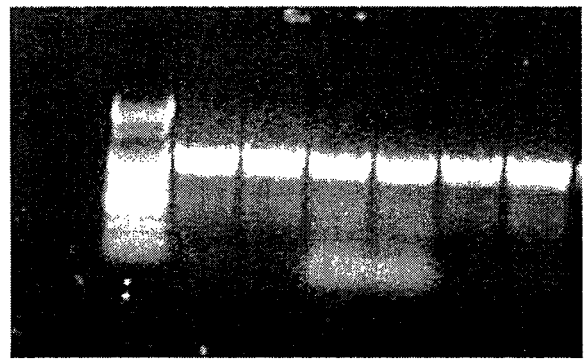

FIG. 4 is a photograph illustrating the results of agarose gel electrophoresis of the reaction product amplified by PCR, in the cases where glycerin is not added to the oligonucleotide, and where the substance is added to the oligonucleotide in varying amounts.

Lane M; molecular weight standards of 1 kb (ladder),
Lanes 1 and 2; control compositions without addition of a substance for preventing the oligonucleotide from being separated and lost,
Lanes 3 and 4; compositions with addition of a 1.0% (v/v) glycerin.
Lanes 5 and 6; compositions with addition of a 0.25% (v/v) glycerin.

Figure 5:
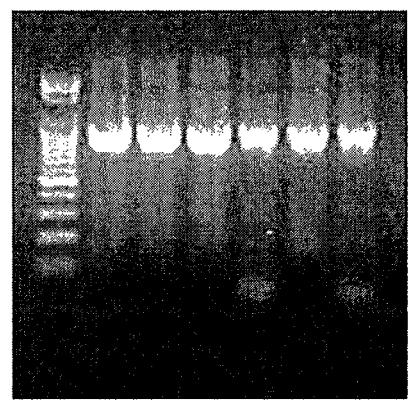

FIG. 5 is a photograph illustrating the results of agarose gel electrophoresis of the reaction product amplified by PCR, in the case where polyoxyethylene sorbitan monolaurate is added to the oligonucleotide composition in varying amounts as a substance for preventing the oligonucleotide from being separated and lost.
Lane M; molecular weight standards of 1 kb (ladder),
Lanes 1, 2 and 3; compositions with addition of a 0.25% (v/v) polyoxyethylene sorbitan monolaurate.
Lanes 4, 5 and 6; compositions with addition of a 1.0% (v/v) polyoxyethylene sorbitan monolaurate.

Figure 6:
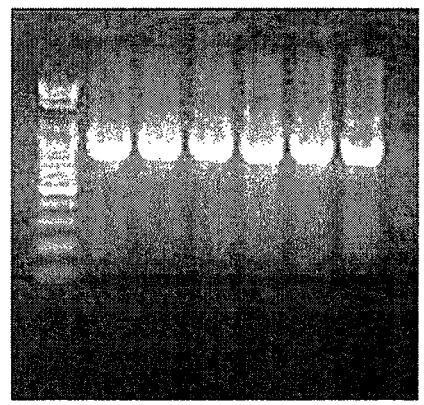

FIG. 6 is a photograph illustrating the results of agarose gel electrophoresis of the reaction product amplified by PCR, in the case where polyethylene glycol (PEG) is added to the oligonucleotide composition in varying amounts as a substance for preventing the oligonucleotide from being separated and lost.
Lane M; molecular weight standards of 1 kb (ladder),
Lanes 1, 2 and 3; compositions with addition of a 0.1% (w/v) PEG,
Lanes 4, 5 and 6; compositions with addition of a 1.0% (w/v) PEG.

EXAMPLES

The present invention will be described in more detail by referring to examples below, which are not intended to limit the present invention.

Effect of Substance for Preventing the Oligonucleotide from Being Separated and Lost on Dried DNA Oligonucleotide

Effect of Polyalcohol

Example 1

Glycerin

A forward oligonucleotide primer having a base sequence represented by SEQ ID NO: 1 (5'-AAT ATG AGC CAG CGG GGA TT-3') and a reverse oligonucleotide primer having a base sequence represented by SEQ ID NO: 2 (5'-CAT CCA GAA AAC GGG CGT AA-3') were chemically synthesized. Thereafter, two sets of oligonucleotide composition, each consisting of five members (totally 10 members), were quantitated using a UV-spectrophotometer to give an OD (optical density) value of 2, and then aliquoted into a polypropylene storage container in portions of 200 µl. 10 µl of a 0.25% (v/v) glycerin solution as a substance for preventing the oligonucleotide from being separated and lost was added thereto, and the container was installed on a vacuum centrifuge, and heated using a halogen lamp. Then, the resultant was dried over 4 hours or longer under a vacuum state below 1 torr or less in order to prepare dried oligonucleotide composition. In order to confirm the presence or absence of the oligonucleotide, ten of the dried oligonucleotide composition were dissolved in 200 µl of ultra pure water and then quantitated using a UV-spectrophotometer. As a result, the OD value was about 2, confirming that there was no loss of the oligonucleotide even after the drying step (Table 1).

TABLE 1

Loss of oligonucleotide from oligonucleotide composition comprising glycerin

| No. | OD before drying | OD after drying | loss of oligonucleotide |
|---|---|---|---|
| 1 | 2 | 1.99 | None |
| 2 | 2 | 1.92 | None |
| 3 | 2 | 2.00 | None |
| 4 | 2 | 2.06 | None |
| 5 | 2 | 2.02 | None |
| 6 | 2 | 1.88 | None |
| 7 | 2 | 1.92 | None |
| 8 | 2 | 2.13 | None |
| 9 | 2 | 2.00 | None |
| 10 | 2 | 1.94 | None |
| average | 2 | 1.98 | |

Examples 2-5

Polyalcohol Other than Glycerin

Experiment was carried out in the same manner as in Example 1, except that 10 µl of a 0.25% (v/v) ethylene glycol, 10 µl of a 0.1% (v/v) glucose, 10 µl of a 0.1% (v/v) sorbitol, or 10 µl of a 0.1% (v/v) mannitol was used as a substance for preventing the oligonucleotide from being separated and lost. As a result, the OD value was about 2, confirming that there was no loss of the oligonucleotide even after the drying step (Tables 2 to 5).

TABLE 2

Loss of oligonucleotide from oligonucleotide composition comprising ethylene glycol

| No. | OD before drying | OD after drying | loss of oligonucleotide |
|---|---|---|---|
| 1 | 2 | 1.99 | None |
| 2 | 2 | 1.97 | None |
| 3 | 2 | 2.02 | None |
| 4 | 2 | 1.79 | None |
| 5 | 2 | 2.00 | None |
| 6 | 2 | 1.88 | None |
| 7 | 2 | 1.95 | None |
| 8 | 2 | 1.91 | None |
| 9 | 2 | 1.90 | None |
| 10 | 2 | 2.01 | None |
| average | 2 | 1.94 | |

TABLE 3

Loss of oligonucleotide from oligonucleotide composition comprising glucose

| No. | OD before drying | OD after drying | loss of oligonucleotide |
|---|---|---|---|
| 1 | 2 | 2.00 | None |
| 2 | 2 | 2.02 | None |
| 3 | 2 | 2.01 | None |
| 4 | 2 | 2.06 | None |
| 5 | 2 | 1.88 | None |
| 6 | 2 | 1.83 | None |
| 7 | 2 | 1.88 | None |
| 8 | 2 | 1.99 | None |

TABLE 3-continued

Loss of oligonucleotide from oligonucleotide composition comprising glucose

| No. | OD before drying | OD after drying | loss of oligonucleotide |
|---|---|---|---|
| 9 | 2 | 1.92 | None |
| 10 | 2 | 2.05 | None |
| average | 2 | 1.96 | |

TABLE 4

Loss of oligonucleotide from oligonucleotide composition comprising sorbitol

| No. | OD before drying | OD after drying | loss of oligonucleotide |
|---|---|---|---|
| 1 | 2 | 2.01 | None |
| 2 | 2 | 2.02 | None |
| 3 | 2 | 1.82 | None |
| 4 | 2 | 1.97 | None |
| 5 | 2 | 1.77 | None |
| 6 | 2 | 1.83 | None |
| 7 | 2 | 1.82 | None |
| 8 | 2 | 1.88 | None |
| 9 | 2 | 1.96 | None |
| 10 | 2 | 1.71 | None |
| average | 2 | 1.88 | |

TABLE 5

Loss of oligonucleotide from oligonucleotide composition comprising mannitol

| No. | OD before drying | OD after drying | loss of oligonucleotide |
|---|---|---|---|
| 1 | 2 | 1.82 | None |
| 2 | 2 | 1.87 | None |
| 3 | 2 | 1.85 | None |
| 4 | 2 | 1.82 | None |
| 5 | 2 | 1.95 | None |
| 6 | 2 | 1.79 | None |
| 7 | 2 | 1.79 | None |
| 8 | 2 | 1.89 | None |
| 9 | 2 | 1.77 | None |
| 10 | 2 | 1.91 | None |
| average | 2 | 1.85 | |

Effect of Oligosaccharide

Example 6

Isomalto Oligosaccharide

Experiment was carried out in the same manner as in Example 1 except that 10 μl of a 0.25% (v/v) isomalto oligosaccharide was used as a substance for preventing the oligonucleotide from being separated and lost. As a result, the OD value was about 2, confirming that there was no loss of the oligonucleotide even after the drying step (Table 6).

TABLE 6

Loss of oligonucleotide from oligonucleotide composition comprising isomalto oligosaccharide

| No. | OD before drying | OD after drying | loss of oligonucleotide |
|---|---|---|---|
| 1 | 2 | 1.93 | None |
| 2 | 2 | 1.95 | None |
| 3 | 2 | 1.91 | None |

TABLE 6-continued

Loss of oligonucleotide from oligonucleotide composition comprising isomalto oligosaccharide

| No. | OD before drying | OD after drying | loss of oligonucleotide |
|---|---|---|---|
| 4 | 2 | 1.98 | None |
| 5 | 2 | 1.94 | None |
| 6 | 2 | 1.97 | None |
| 7 | 2 | 1.96 | None |
| 8 | 2 | 1.99 | None |
| 9 | 2 | 1.92 | None |
| 10 | 2 | 2.05 | None |
| average | 2 | 1.96 | |

Example 7

Oligosaccharide Other than Isomalto Oligosaccharide

Experiment was carried out in the same manner as in Example 6 except that 10 μl of a 0.05% (v/v) malto oligosaccharide was used as a substance for preventing the oligonucleotide from being separated and lost. As a result, the OD value was about 2, confirming that there was no loss of the oligonucleotide even after the drying step (Table 7).

TABLE 7

Loss of oligonucleotide from oligonucleotide composition comprising malto oligosaccharide

| No. | OD before drying | OD after drying | loss of oligonucleotide |
|---|---|---|---|
| 1 | 2 | 1.74 | None |
| 2 | 2 | 1.77 | None |
| 3 | 2 | 2.04 | None |
| 4 | 2 | 2.06 | None |
| 5 | 2 | 1.98 | None |
| 6 | 2 | 1.78 | None |
| 7 | 2 | 1.90 | None |
| 8 | 2 | 2.00 | None |
| 9 | 2 | 2.01 | None |
| 10 | 2 | 1.97 | None |
| average | 2 | 1.92 | |

Effect of Nonionic Surfactant

Example 8

Polyoxyethylene Sorbitan Monolaurate

Experiment was carried out in the same manner as in Example 1 except that 10 μl of a 0.25% (v/v) polyoxyethylene sorbitan monolaurate was used as a substance for preventing the oligonucleotide from being separated and lost. As a result, the OD value was about 2, confirming that there was no loss of the oligonucleotide even after the drying step (Table 8).

TABLE 8

Loss of oligonucleotide from oligonucleotide composition comprising polyoxyethylene sorbitan monolaurate

| No. | OD before drying | OD after drying | loss of oligonucleotide |
|---|---|---|---|
| 1 | 2 | 2.01 | None |
| 2 | 2 | 1.94 | None |
| 3 | 2 | 1.69 | None |
| 4 | 2 | 2.00 | None |

TABLE 8-continued

Loss of oligonucleotide from oligonucleotide composition comprising polyoxyethylene sorbitan monolaurate

| No. | OD before drying | OD after drying | loss of oligonucleotide |
|---|---|---|---|
| 5 | 2 | 1.94 | None |
| 6 | 2 | 2.05 | None |
| 7 | 2 | 1.94 | None |
| 8 | 2 | 1.89 | None |
| 9 | 2 | 2.06 | None |
| 10 | 2 | 1.91 | None |
| average | 2 | 1.94 | |

Examples 9-11

Nonionic Surfactant Other than Polyoxyethylene Sorbitan Monolaurate

Experiment was carried out in the same manner as in Example 8, except that 10 µl of a 0.25% (v/v) sorbitan monolaurate, 10 µl of a 0.1% (w/v) methyl glucoside, or 10 µl of a 0.1% (w/v) octyl glucoside was used as a substance for preventing the oligonucleotide from being separated and lost. As a result, the OD value was about 2, confirming that there was no loss of the oligonucleotide even after the drying step (Tables 9 to 11).

TABLE 9

Loss of oligonucleotide from oligonucleotide composition comprising sorbitan monolaurate

| No. | OD before drying | OD after drying | loss of oligonucleotide |
|---|---|---|---|
| 1 | 2 | 1.98 | None |
| 2 | 2 | 2.00 | None |
| 3 | 2 | 1.91 | None |
| 4 | 2 | 1.86 | None |
| 5 | 2 | 1.82 | None |
| 6 | 2 | 1.83 | None |
| 7 | 2 | 1.85 | None |
| 8 | 2 | 1.75 | None |
| 9 | 2 | 1.92 | None |
| 10 | 2 | 2.01 | None |
| average | 2 | 1.89 | |

TABLE 10

Loss of oligonucleotide from oligonucleotide composition comprising methyl glucoside

| No. | OD before drying | OD after drying | loss of oligonucleotide |
|---|---|---|---|
| 1 | 2 | 1.99 | None |
| 2 | 2 | 2.13 | None |
| 3 | 2 | 1.91 | None |
| 4 | 2 | 1.75 | None |
| 5 | 2 | 1.75 | None |
| 6 | 2 | 1.79 | None |
| 7 | 2 | 1.89 | None |
| 8 | 2 | 1.83 | None |
| 9 | 2 | 1.77 | None |
| 10 | 2 | 1.86 | None |
| average | 2 | 1.87 | |

TABLE 11

Loss of oligonucleotide from oligonucleotide composition comprising octyl glucoside

| No. | OD before drying | OD after drying | loss of oligonucleotide |
|---|---|---|---|
| 1 | 2 | 1.94 | None |
| 2 | 2 | 1.90 | None |
| 3 | 2 | 1.78 | None |
| 4 | 2 | 1.77 | None |
| 5 | 2 | 1.73 | None |
| 6 | 2 | 1.87 | None |
| 7 | 2 | 1.87 | None |
| 8 | 2 | 1.86 | None |
| 9 | 2 | 1.96 | None |
| 10 | 2 | 1.90 | None |
| average | 2 | 1.86 | |

Effect of Water Soluble Polymer

Example 12

Polyethylene Glycol

Experiment was carried out in the same manner as in Example 1 except that 10 µl of a 0.1% (w/v) polyethylene glycol (MW: 8,000) was used as a substance for preventing the oligonucleotide from being separated and lost. As a result, the OD value was about 2, confirming that there was no loss of the oligonucleotide even after the drying step (Table 12).

TABLE 12

Loss of oligonucleotide from oligonucleotide composition comprising polyethylene glycol

| No. | OD before drying | OD after drying | loss of oligonucleotide |
|---|---|---|---|
| 1 | 2 | 2.14 | None |
| 2 | 2 | 1.93 | None |
| 3 | 2 | 2.01 | None |
| 4 | 2 | 2.06 | None |
| 5 | 2 | 2.00 | None |
| 6 | 2 | 2.06 | None |
| 7 | 2 | 2.03 | None |
| 8 | 2 | 1.98 | None |
| 9 | 2 | 1.94 | None |
| 10 | 2 | 2.03 | None |
| average | 2 | 2.02 | |

Examples 13-15

Water Soluble Polymer Other than Polyethylene Glycol

Experiment was carried out in the same manner as in Example 12, except that 10 µl of a 0.01% (w/v) polyvinyl alcohol, 10 µl of a 0.25% (v/v) polyacrylic acid, or 10 µl of a 0.25% (v/v) polymethacrylic acid was used as a substance for preventing the oligonucleotide from being separated and lost. As a result, the OD value was about 2, confirming that there was no loss of the oligonucleotide even after the drying step (Tables 13 to 15).

TABLE 13

Loss of oligonucleotide from oligonucleotide composition comprising polyvinyl alcohol

| No. | OD before drying | OD after drying | loss of oligonucleotide |
|---|---|---|---|
| 1 | 2 | 1.97 | None |
| 2 | 2 | 1.91 | None |
| 3 | 2 | 1.74 | None |
| 4 | 2 | 1.84 | None |
| 5 | 2 | 1.81 | None |
| 6 | 2 | 1.73 | None |
| 7 | 2 | 1.94 | None |
| 8 | 2 | 2.08 | None |
| 9 | 2 | 2.11 | None |
| 10 | 2 | 1.13 | None |
| average | 2 | 1.93 | |

TABLE 14

Loss of oligonucleotide from oligonucleotide composition comprising polyacrylic acid

| No. | OD before drying | OD after drying | loss of oligonucleotide |
|---|---|---|---|
| 1 | 2 | 2.00 | None |
| 2 | 2 | 1.97 | None |
| 3 | 2 | 2.00 | None |
| 4 | 2 | 1.96 | None |
| 5 | 2 | 1.94 | None |
| 6 | 2 | 1.67 | None |
| 7 | 2 | 1.83 | None |
| 8 | 2 | 1.88 | None |
| 9 | 2 | 1.95 | None |
| 10 | 2 | 2.02 | None |
| average | 2 | 1.92 | |

TABLE 15

Loss of oligonucleotide from oligonucleotide composition comprising polymethacrylic acid

| No. | OD before drying | OD after drying | loss of oligonucleotide |
|---|---|---|---|
| 1 | 2 | 1.83 | None |
| 2 | 2 | 2.07 | None |
| 3 | 2 | 2.00 | None |
| 4 | 2 | 2.08 | None |
| 5 | 2 | 1.87 | None |
| 6 | 2 | 1.91 | None |
| 7 | 2 | 1.92 | None |
| 8 | 2 | 1.85 | None |
| 9 | 2 | 1.82 | None |
| 10 | 2 | 1.91 | None |
| average | 2 | 1.93 | |

Effect of Protein

Example 16

Bovine Serum Albumin

Experiment was carried out in the same manner as in Example 1 except that 10 µl of a 0.05% (w/v) bovine serum albumin (BSA) was used as a substance for preventing the oligonucleotide from being separated and lost. As a result, the OD value was about 2, confirming that there was no loss of the oligonucleotide even after the drying step (Table 16).

TABLE 16

Loss of oligonucleotide from oligonucleotide composition comprising bovine serum albumin (BSA)

| No. | OD before drying | OD after drying | loss of oligonucleotide |
|---|---|---|---|
| 1 | 2 | 1.88 | None |
| 2 | 2 | 1.83 | None |
| 3 | 2 | 2.00 | None |
| 4 | 2 | 2.10 | None |
| 5 | 2 | 2.08 | None |
| 6 | 2 | 1.99 | None |
| 7 | 2 | 2.07 | None |
| 8 | 2 | 1.92 | None |
| 9 | 2 | 1.88 | None |
| 10 | 2 | 1.78 | None |
| average | 2 | 1.95 | |

Example 17

Protein Other than Bovine Serum Albumin

Experiment was carried out in the same manner as in Example 16 except that 10 µl of a 0.01% (v/v) gelatin was used as a substance for preventing the oligonucleotide from being separated and lost. As a result, the OD value was about 2, confirming that there was no loss of the oligonucleotide even after the drying step (Table 17).

TABLE 17

Loss of oligonucleotide from oligonucleotide composition comprising gelatin

| No. | OD before drying | OD after drying | loss of oligonucleotide |
|---|---|---|---|
| 1 | 2 | 1.74 | None |
| 2 | 2 | 1.89 | None |
| 3 | 2 | 1.95 | None |
| 4 | 2 | 1.95 | None |
| 5 | 2 | 1.83 | None |
| 6 | 2 | 1.90 | None |
| 7 | 2 | 1.88 | None |
| 8 | 2 | 1.82 | None |
| 9 | 2 | 1.98 | None |
| 10 | 2 | 1.79 | None |
| average | 2 | 1.87 | |

Comparative Example 1

For comparison, oligonucleotide composition without addition of a substance for preventing the oligonucleotide from being separated and lost was aliquoted into ten storage containers in portions of 200 µl to give an OD value of 2. Then, the aliquoted oligonucleotide composition was dried on a dryer for 4 hours to prepare a dried oligonucleotide product. Ten of the prepared products were dissolved in 200 µl of ultra pure water and then quantitated using a UV-spectrophotometer. As a result, the OD value was much less than 2 in some cases, confirming that there was partial loss of oligonucleotide (Table 18).

TABLE 18

Loss of oligonucleotide which does not contain a substance for preventing the oligonucleotide from being separated and lost

| No. | OD before drying | OD after drying | loss of oligonucleotide |
|---|---|---|---|
| 1 | 2 | 0.11 | Loss |
| 2 | 2 | 2.06 | None |

TABLE 18-continued

Loss of oligonucleotide which does not contain a substance
for preventing the oligonucleotide from being separated and lost

| No. | OD before drying | OD after drying | loss of oligonucleotide |
|---|---|---|---|
| 3 | 2 | 1.94 | None |
| 4 | 2 | 2.13 | None |
| 5 | 2 | 0.07 | Loss |
| 6 | 2 | 2.06 | None |
| 7 | 2 | 0.95 | Loss |
| 8 | 2 | 1.44 | Loss |
| 9 | 2 | 0.22 | Loss |
| 10 | 2 | 1.88 | None |
| average | 2 | 1.28 | |

Effect of Substance for Preventing the
Oligonucleotide from being Separated and Lost on
Dried RNA Oligonucleotide Example 18

Effect of Polyalcohol

Experiment was carried out with addition of 10 µl of a 0.25% (v/v) glycerin in the same manner as in Example 1, except that a sense siRNA oligonucleotide having a base sequence represented by SEQ ID NO: 3 (5'-CCA AGU AAC UCU CCU CAA AUA dTdT-3') and an antisense siRNA oligonucleotide having a base sequence represented by SEQ ID NO: 4 (5'-UAU UUG AGG AGA GUU ACU UGG dTdT-3') were used as the oligonucleotide primers. As a result, the OD value was about 2, confirming that there was no loss of the siRNA oligonucleotide even after the drying step (Table 19). Moreover, in the case where ethylene glycol, glucose, sorbitol or mannitol was used as a polyalcohol instead of glycerin, the similar results were obtained.

TABLE 19

Loss of siRNA oligonucleotide comprising glycerin

| No. | OD before drying | OD after drying | loss of oligonucleotide |
|---|---|---|---|
| 1 | 2 | 1.83 | None |
| 2 | 2 | 1.91 | None |
| 3 | 2 | 1.94 | None |
| 4 | 2 | 1.90 | None |
| 5 | 2 | 1.97 | None |
| 6 | 2 | 1.94 | None |
| 7 | 2 | 1.99 | None |
| 8 | 2 | 2.03 | None |
| 9 | 2 | 1.84 | None |
| 10 | 2 | 1.90 | None |
| average | 2 | 1.93 | |

Example 19

Effect of Oligosaccharides

Experiment was carried out in the same manner as in Example 18, except that 10 µl of a 0.25% (v/v) isomalto oligosaccharide was used as a substance for preventing the oligonucleotide from being separated and lost. As a result, the OD value was about 2, confirming that there was no loss of the siRNA oligonucleotide even after the drying step (Table 20). Moreover, in the case where malto oligosaccharide was used as an oligosaccharide instead of isomalto oligosaccharide, the similar results were obtained.

TABLE 20

Loss of siRNA oligonucleotide comprising isomalto oligosaccharide

| No. | OD before drying | OD after drying | loss of oligonucleotide |
|---|---|---|---|
| 1 | 2 | 1.68 | None |
| 2 | 2 | 1.91 | None |
| 3 | 2 | 1.86 | None |
| 4 | 2 | 2.03 | None |
| 5 | 2 | 2.16 | None |
| 6 | 2 | 1.72 | None |
| 7 | 2 | 1.78 | None |
| 8 | 2 | 1.77 | None |
| 9 | 2 | 1.73 | None |
| 10 | 2 | 1.85 | None |
| average | 2 | 1.85 | |

Example 20

Effect of Nonionic Surfactant

Experiment was carried out in the same manner as in Example 18, except that 10 µl of a 0.25% (v/v) polyoxyethylene sorbitan monolaurate was used as a substance for preventing the oligonucleotide from being separated and lost. As a result, the OD value was about 2, confirming that there was no loss of the siRNA oligonucleotide even after the drying step (Table 21). Moreover, in the case where sorbitan monolaurate, methyl glucoside, or octyl glucoside was used as a nonionic surfactant instead of polyoxyethylene sorbitan monolaurate, the similar results were obtained.

TABLE 21

Loss of siRNA oligonucleotide comprising
polyoxyethylene sorbitan monolaurate

| No. | OD before drying | OD after drying | loss of oligonucleotide |
|---|---|---|---|
| 1 | 2 | 2.11 | None |
| 2 | 2 | 2.00 | None |
| 3 | 2 | 2.05 | None |
| 4 | 2 | 2.03 | None |
| 5 | 2 | 1.83 | None |
| 6 | 2 | 1.82 | None |
| 7 | 2 | 1.75 | None |
| 8 | 2 | 1.77 | None |
| 9 | 2 | 2.05 | None |
| 10 | 2 | 1.80 | None |
| average | 2 | 1.92 | |

Example 21

Effect of Water Soluble Polymer

Experiment was carried out in the same manner as in Example 18, except that 10 µl of a 0.1% (w/v) polyethylene glycol (MW: 8,000) was used as a substance for preventing the oligonucleotide from being separated and lost. As a result, the OD value was about 2, confirming that there was no loss of the siRNA oligonucleotide even after the drying step (Table 22). Moreover, in the case where polyvinyl alcohol, polyacrylic acid, or polymethacrylic acid was used as a water soluble polymer instead of polyethylene glycol, the similar results were obtained.

TABLE 22

Loss of siRNA oligonucleotide comprising polyethylene glycol

| No. | OD before drying | OD after drying | loss of oligonucleotide |
|---|---|---|---|
| 1 | 2 | 1.93 | None |
| 2 | 2 | 2.08 | None |
| 3 | 2 | 1.86 | None |
| 4 | 2 | 1.83 | None |
| 5 | 2 | 1.93 | None |
| 6 | 2 | 1.72 | None |
| 7 | 2 | 1.65 | None |
| 8 | 2 | 1.73 | None |
| 9 | 2 | 1.67 | None |
| 10 | 2 | 1.72 | None |
| average | 2 | 1.81 | |

Example 22

Effect of Protein

Experiment was carried out in the same manner as in Example 18, except that 10 µl of a 0.05% (w/v) bovine serum albumin was used as a substance for preventing the oligonucleotide from being separated and lost. As a result, the OD value was about 2, confirming that there was no loss of the siRNA oligonucleotide even after the drying step (Table 23). Moreover, in the case where gelatin was used as a protein instead of bovine serum albumin, the similar results were obtained.

TABLE 23

Loss of siRNA oligonucleotide comprising bovine serum albumin

| No. | OD before drying | OD after drying | loss of oligonucleotide |
|---|---|---|---|
| 1 | 2 | 1.98 | None |
| 2 | 2 | 2.03 | None |
| 3 | 2 | 1.82 | None |
| 4 | 2 | 1.88 | None |
| 5 | 2 | 1.78 | None |
| 6 | 2 | 1.70 | None |
| 7 | 2 | 1.67 | None |
| 8 | 2 | 1.86 | None |
| 9 | 2 | 1.70 | None |
| 10 | 2 | 1.67 | None |
| average | 2 | 1.81 | |

Determination of an Effect of Substance for Preventing the Oligonucleotide from being Separated and Lost and Non-Reactive Dye Substance on PCR Example 23

Effect of Polyalcohol

In order to confirm whether a substance for preventing the oligonucleotide from being separated and lost gives any effect on PCR process or not, a forward oligonucleotide primer having a base sequence represented by SEQ ID NO: 1 and a reverse oligonucleotide primer having a base sequence represented by SEQ ID NO: 2 were synthesized. The primer pairs give a reaction product of a size of 1 kb using a lambda DNA as a template. 10 pmol of each of the oligonucleotide primers were mixed, and 10 µl of a 0.25% (v/v) glycerin solution as a substance for preventing the oligonucleotide from being separated and lost, and 2 µl of a 0.01% (v/v) xylene cyanole as a non-reactive dye substance were added to the mixture. The resultant was dried to prepare dried oligonucleotide composition. For comparison, a dried oligonucleotide composition which does not contain a substance for preventing the oligonucleotide from being separated and lost and a non-reactive dye substance was used as a control. 10 mM Tris-HCl (pH 8.3), 40 mM KCl, 1.5 mM MgCl$_2$, 1 mM DTT, 50 mg/ml BSA, 250 µM of four kinds of dNTPs and 1 ng lambda DNA template (purchased from SIB, Russia) and 1 unit of a DNA polymerase (Taq DNA polymerase) were mixed to carry out PCR. The concentration and amount of the components indicate the final concentration and amount of each component contained in 0.05 ml of the reaction solution, respectively. PCR was done by performing 30 cycles of denaturation (1 min, 94° C.), annealing (1 min, 54° C.), and extension (1 min, 72° C.) for amplification of DNA. The amplified PCR products were divided into three sets, and subject to 1% (w/v) agarose gel electrophoresis.

Figure 1:
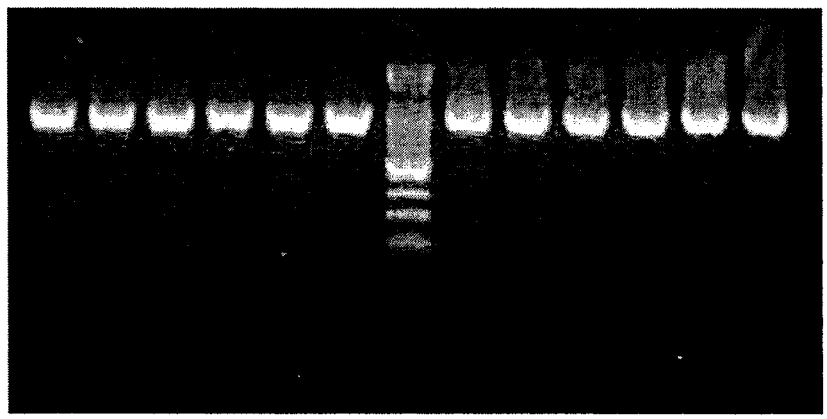
FIG. 1 is a photograph illustrating the results of agarose gel electrophoresis of the reaction product amplified by PCR, in the cases where a substance for preventing the oligonucleotide from being separated and lost is not added to the oligonucleotide, and where glycerin or polyoxyethylene sorbitan monolaurate is added to the oligonucleotide.

As a result, DNA with a size of 1 kb was clearly amplified in Lanes 1, 2 and 3 in which a substance for preventing the oligonucleotide from being separated and lost and a non-reactive dye substance were not added, and Lanes 4, 5 and 6 in which a 0.25% (v/v) glycerin solution and 0.01% xylene cyanole solution were added (FIG. 1). Thus, it was confirmed that in the case of a composition with an addition of glycerin as a substance for preventing the oligonucleotide from being separated and lost, and xylene cyanole as a non-reactive dye substance, any effect on PCR was not observed. Further, in the case where ethylene glycol, glucose, sorbitol or mannitol was used as a polyalcohol instead of glycerin, and xylene cyanole was used as a non-reactive dye substance, any effect on PCR was not observed, similar to that of the case in which glycerin was used.

Example 24

Effect of Nonionic Surfactant

PCR was carried out under the same conditions as in Example 23, except that 10 µl of polyoxyethylene sorbitan monolaurate was added instead of glycerin as a substance for preventing the oligonucleotide from being separated and lost. The prepared PCR product was subject to electrophoresis. As a result, DNA with a size of 1 kb was clearly amplified in Lanes 7, 8 and 9 in which a substance for preventing the oligonucleotide from being separated and lost and a non-reactive dye substance were not added, and Lanes 10, 11 and 12 in which a 0.25% (v/v) polyoxyethylene sorbitan monolaurate and xylene cyanole as a non-reactive dye substance were added (FIG. 1). Thus, it was confirmed that in the case of a composition with addition of polyoxyethylene sorbitan monolaurate as a substance for preventing the oligonucleotide from being separated and lost, and xylene cyanole as a non-reactive dye substance, any effect on PCR was not observed. Further, in the cases where sorbitan monolaurate, methyl glucoside or octyl glucoside was used as a nonionic surfactant instead of polyoxyethylene sorbitan monolaurate, and xylene cyanole was used as a non-reactive dye substance, any effect on PCR was not observed, similar to that of the case in which polyoxyethylene sorbitan monolaurate was added.

Example 25

Effect of Oligosaccharide

PCR was carried out under the same conditions as in Example 23, except that 10 µl of isomalto oligosaccharide was added instead of glycerin as a substance for preventing the oligonucleotide from being separated and lost. The prepared PCR product was subject to electrophoresis. As a result, DNA with a size of 1 kb was clearly amplified in Lanes 1, 2 and 3 in which a substance for preventing the oligonucleotide from being separated and lost and a non-reactive dye substance were not added, and Lanes 4, 5 and 6 in which a 0.25% (v/v) isomalto oligosaccharide and xylene cyanole as a non-reactive dye substance were added (FIG. 2). Thus, it was confirmed that in the case of a composition with addition of isomalto oligosaccharide a substance for preventing the oligonucleotide from being separated and lost, and xylene cyanole as a non-reactive dye substance, any effect on PCR was not observed. Further, in the cases where malto oligosaccharide was used as an oligosaccharide instead of isomalto oligosaccharide, and xylene cyanole was used as a non-reactive dye substance, any effect on PCR was not observed, similar to that of the case in which isomalto oligosaccharide was added.

Example 26

Effect of Water Soluble Polymer

PCR was carried out under the same conditions as in Example 23, except that 10 µl of a 0.1% (w/v) polyethylene glycol was added instead of glycerin as a substance for preventing the oligonucleotide from being separated and lost. The prepared PCR product was subject to electrophoresis. As a result, DNA with a size of 1 kb was clearly amplified in Lanes 7, 8 and 9 in which a substance for preventing the oligonucleotide from being separated and lost and a non-reactive dye substance were not added, and Lanes 10, 11 and 12 in which a 0.1% (w/v) polyethylene glycol and xylene cyanole as a non-reactive dye substance were added (FIG. 2). Thus, it was confirmed that in the case of a composition with addition of polyethylene glycol as a substance for preventing the oligonucleotide from being separated and lost, and xylene cyanole as a non-reactive dye substance, any effect on PCR was not observed. Further, in the cases where polyvinyl alcohol, polyacrylic acid, or polymethacrylic acid was used as a water soluble polymer instead of polyethylene glycol, and xylene cyanole was used as a non-reactive dye substance, any effect on PCR was not observed, similar to that of the case in which polyethylene glycol was added.

Example 27

Effect of Protein

PCR was carried out under the same conditions as in Example 23, except that 10 µl of a 0.05% (w/v) bovine serum albumin was added instead of glycerin as a substance for preventing the oligonucleotide from being separated and lost. The prepared PCR product was subject to electrophoresis. As a result, DNA with a size of 1 kb was clearly amplified in Lanes 1, 2 and 3 in which a substance for preventing the oligonucleotide from being separated and lost and a non-reactive dye substance were not added, and Lanes 4, 5 and 6 in which a 0.1% (w/v) bovine serum albumin and xylene cyanole as a non-reactive dye substance were added (FIG. 3). Thus, it was confirmed that in the case of a composition with addition of bovine serum albumin as a substance for preventing the oligonucleotide from being separated and lost, and xylene cyanole as a non-reactive dye substance, any effect on PCR was not observed. Further, in the cases where gelatin was used as a protein instead of bovine serum albumin, and xylene cyanole was used as a non-reactive dye substance, any effect on PCR was not observed, similar to that of the case in which bovine serum albumin was added.

Determination of an Effect of the Amount of Substance for Preventing the Oligonucleotide from being Separated and Lost on PCR Effect of Polyalcohol Example 28

Glycerin

In order to confirm the effect of the amount of glycerin to be added as a substance for preventing the oligonucleotide from being separated and lost on PCR, comparative experiments were carried out with regard to the case in which glycerin was not added to the primer in the composition of Example 1, and the cases in which glycerin was added in a small amount or a large amount, respectively. Specifically, after preparing six containers, glycerin was not added to two of them, 10 µl of a 0.25% (v/v) glycerin was added to two of them, and 10 µl of a 1.0% (v/v) glycerin was added to two of them, respectively. Then, PCR was carried out under the same conditions as in Example 23. After electrophoresis of the six sets of the PCR products, it was found that in the case in which an excessive amount of glycerin was added (addition of 10 µl of a 1.0% (v/v) glycerin), bands other than 1 kb in size were observed, showing that PCR was affected (FIG. 4). Further, in the case where ethylene glycol, glucose, sorbitol or mannitol was used as a polyalcohol instead of glycerin, the similar results were obtained.

Effect of Nonionic Surfactant

Example 29

Polyoxyethylene Sorbitan Monolaurate

In order to confirm the effect of the amount of polyoxyethylene sorbitan monolaurate to be added as a substance for preventing the oligonucleotide from being separated and lost on PCR, comparative experiments were carried out with regard to the cases in which polyoxyethylene sorbitan monolaurate was added in a small amount or a large amount, respectively. Specifically, after preparing six containers, 10 µl of a 0.25% (v/v) polyoxyethylene sorbitan monolaurate was added to three of them, and 10 µl of a 1.0% (v/v) polyoxyethylene sorbitan monolaurate was added to three of them, respectively. Then, PCR was carried out under the same conditions as in Example 23. After electrophoresis of the six sets of the PCR products, it was found that in the case in which an excessive amount of polyoxyethylene sorbitan monolaurate was added (addition of 10 µl of a 1.0% (v/v) polyoxyethylene sorbitan monolaurate), bands other than 1 kb in size were observed and the size of the main band is small, showing that PCR was affected (FIG. 5). Further, in the case where sorbitan monolaurate, methyl glucoside or octyl glucoside was used as a nonionic surfactant instead of polyoxyethylene sorbitan monolaurate, the similar results were obtained.

Effect of Water Soluble Polymer

Example 30

Polyethylene Glycol

The same experiment was carried out under the same conditions as in Example 28, except that polyethylene glycol was added as a substance for preventing the oligonucleotide from being separated and lost. As a result, in the case in which an excessive amount of polyethylene glycol was added (addition of 10 µl of a 1.0% (w/v) polyethylene glycol), bands other than 1 kb in size were observed, showing that PCR was affected (FIG. 6). Further, in the case where polyvinyl alcohol, polyacrylic acid or polymethacrylic acid was used as a water soluble polymer instead of polyethylene glycol, the similar results were obtained.

Effect of Oligosaccharide

Example 31

Isomalto Oligosaccharide

The same experiment was carried out under the same conditions as in Example 28, except that isomalto oligosaccharide was added as a substance for preventing the oligonucleotide from being separated and lost. As a result, in the case in which an excessive amount of isomalto oligosaccharide was added (addition of 10 µl of a 1.0% (v/v) isomalto oligosaccharide), bands other than 1 kb in size were observed, showing that PCR was affected. Further, in the case where malto oligosaccharide was used as an oligosaccharide instead of isomalto oligosaccharide, the similar results were obtained.

Effect of Protein

Example 32

Bovine Serum Albumin

The same experiment was carried out under the same conditions as in Example 28, except that bovine serum albumin was added as a substance for preventing the oligonucleotide from being separated and lost. As a result, in the case in which an excessive amount of bovine serum albumin was added (addition of 10 µl of a 1.0% (w/v) bovine serum albumin), bands other than 1 kb in size were observed, showing that PCR was affected. Further, in the case where gelatin was used as a protein instead of bovine serum albumin, the similar results were obtained.

INDUSTRIAL APPLICABILITY

As described above, according to the present invention, the oligonucleotide can be prevented from being separated and lost during a drying step, and even if the oligonucleotide is separated and lost, it can be easily checked with naked eyes, thereby remarkably reducing the failure rate during manufacturing process.

Although the preferred embodiment of the present invention has been described, it will be understood by those skilled in the art that the present invention should not be limited to the described preferred embodiment, but various changes and modifications can be made within the spirit and scope of the present invention as defined by the appended claims.

SEQUENCE LISTING

Sequence listing is attached herewith.

What is claimed is:

1. A composition for preventing the loss of oligonucleotide from a storage container consisting of a mixed solution consisting of an oligonucleotide, polyalcohol and water for preventing the oligonucleotide from being separated and lost, and optionally one or more non-reactive dye substance selected from the group consisting of bromophenol blue, xylene cyanole, bromocresol red and cresol red,
    wherein said mixed solution contains said polyalcohol in an amount of 0.01 to 5 parts by weight based on 100 parts by weight of the oligonucleotide, and
    wherein said composition is adhesive to said storage container after said solution is aliquoted into and dried in said storage container to prevent the loss of dried oligonucleotide from said storage container, and
    wherein said polyalcohol is chemically non-reactive with the oligonucleotide, and does not give substantive influence on PCR reaction.

2. The composition according to claim 1, wherein the polyalcohol is one or more selected from the group consisting of ethylene glycol, glycerin, threitol, arabitol, glucose, mannitol, galactitol and sorbitol.

3. The composition according to claim 2, wherein the glycerin is contained in an amount of 0.01 to 0.1 parts by weight based on 100 parts by weight of the oligonucleotide.

4. The composition according to claim 1, the oligonucleotide is a DNA oligonucleotide, RNA oligonucleotide, siRNA oligonucleotide, or combinations thereof.

5. The composition according to claim 1, wherein the non-reactive dye substance is contained in an amount of 1 ppm to 10,000 ppm based on the oligonucleotide.

6. A method of producing the oligonucleotide composition of claim 1, consisting of the step of:

1) preparing a mixed solution consisting of an oligonucleotide, polyalcohol and water for preventing the oligonucleotide from being separated and lost, and optionally one or more non-reactive dye substance selected from the group consisting of bromophenol blue, xylene cyanole, bromocresol red and cresol red.

7. The method according to claim 6, wherein the step is performed by
    i) preparing oligonucleotide composition consisting of an oligonucleotide and water,
    ii) adding a polyalcohol for preventing the oligonucleotide from being separated and lost to the oligonucleotide composition to make a mixed solution consisting of an oligonucleotide, polyalcohol and water; and
    iii) aliquoting predetermined amount of the mixed solution into a synthetic resin container.

8. The method according to claim 6, wherein the synthetic resin container is in a shape of a plate, tube or bottle.

9. The method according to claim 6, wherein the step is performed by
    i) preparing oligonucleotide composition consisting of an oligonucleotide and water,
    ii) aliquoting predetermined amount of the oligonucleotide composition into a synthetic resin container; and
    iii) adding a polyalcohol for preventing the oligonucleotide from being separated and lost to synthetic resin container.

10. The method according to claim 9, wherein the synthetic resin container is in a shape of a plate, tube, or bottle.

11. The method according to claim 6, wherein the non-reactive dye substance is contained in an amount of 1 ppm to 1,000 ppm based on the oligonucleotide.

* * * * *